(12) United States Patent
Mikumo et al.

(10) Patent No.: US 7,189,355 B2
(45) Date of Patent: Mar. 13, 2007

(54) INDICATOR FOR PLASMA STERILIZATION

(76) Inventors: Masao Mikumo, C/O Hogy Medical Co., Ltd., 12-4, Yushima 1-chome, Bunkyo-ku, Tokyo 113-0034 (JP); Kenji Kazama, C/O Hogy Medical Co., Ltd., 12-4, Yushima 1-chome, Bunkyo-ku, Tokyo 113-0034 (JP); Yoshio Jo, C/O Hogy Medical Co., Ltd., 12-4, Yushima 1-chome, Bunkyo-ku, Tokyo 113-0034 (JP)

( * ) Notice: Subject to any disclaimer, the term of this patent is extended or adjusted under 35 U.S.C. 154(b) by 32 days.

(21) Appl. No.: 10/069,848

(22) PCT Filed: Jun. 15, 2001

(86) PCT No.: PCT/JP01/05104

§ 371 (c)(1),
(2), (4) Date: Feb. 28, 2002

(87) PCT Pub. No.: WO02/01205

PCT Pub. Date: Jan. 3, 2002

(65) Prior Publication Data

US 2002/0121629 A1    Sep. 5, 2002

(30) Foreign Application Priority Data

Jun. 29, 2000 (JP) .............................. 2000-197166

(51) Int. Cl.
*G01N 21/78* (2006.01)

(52) U.S. Cl. .................... 422/56; 422/58; 422/61; 422/55; 422/87; 436/1; 436/169; 116/206; 116/207

(58) Field of Classification Search ................. 422/56, 422/58, 61, 28, 87; 436/1, 163, 164, 169; 116/206, 207
See application file for complete search history.

(56) References Cited

U.S. PATENT DOCUMENTS 6,287,518 B1 * 9/2001 Ignacio et al.

FOREIGN PATENT DOCUMENTS

| JP | 5-320616 | 12/1993 |
| JP | 10-30986 | 2/1998 |
| JP | 11-178904 | 7/1999 |

* cited by examiner

*Primary Examiner*—Lyle A. Alexander
(74) *Attorney, Agent, or Firm*—Dilworth & Barrese, LLP

(57) ABSTRACT

The present invention relates to a chemical indicator that is used to determine whether instruments and other products to be sterilized have experienced a sterilization treatment process or to confirm whether sterilization has been efficiently performed, by the color tone change of the indicator when sterilizing medical instruments and other products and the like by a hydrogen peroxide low temperature plasma sterilizing method. The present invention provides an indicator for plasma sterilization, wherein an ink comprising a colorless chromogenic pigment, a coloring assistant, a binder (a binding agent) and a solvent for dissolving these, is applied to or printed on a base material, and wherein a color tone change of the indicator occurs by a hydrogen peroxide low temperature sterilization method.

7 Claims, 16 Drawing Sheets

PIGMENT NAME: LEUCOCRYSTAL VIOLET
MANUFACTURER: TOKYO KASEI KOGYO

PIGMENT NAME: CRYSTAL VIOLET LACTONE
MANUFACTURER: TOKYO KASEI KOGYO

PIGMENT NAME: BLUE-200

MANUFACTURER: HODOGAYA CHEMICAL INDUSTRY

PIGMENT NAME: BLUE-63

MANUFACTURER: YAMAMOTO CHEMICAL

PIGMENT NAME: G-118

MANUFACTURER: YAMAMOTO CHEMICAL

PIGMENT NAME: PSD-HR

MANUFACTURER: NIPPON SODA

PIGMENT NAME: TH-107

MANUFACTURER: HODOGAYA CHEMICAL INDUSTRY

EXAMPLE 1

| (1) PIGMENT (DYE) | PSD-HR : 0.5 |
|---|---|
| (2) COLORING ASSISTANT | TETRAMETHYLTHIURAM MONOSULFIDE : 2.5 |
| (3) DISCOLORATION PREVENTING AGENT | NONE |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 9

EXAMPLE 2

| (1) PIGMENT (DYE) | PSD-HR : 0.5 |
|---|---|
| (2) COLORING ASSISTANT | TETRAETHYLTHIURAM DISULFIDE : 2.5 |
| (3) DISCOLORATION PREVENTING AGENT | NONE |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 10

EXAMPLE 3

| (1) PIGMENT (DYE) | PSD-HR : 0.5 |
|---|---|
| (2) COLORING ASSISTANT | 2-BENZOTHIAZOLYL DIETHYLDITHIOCARBAMATE : 2.5 |
| (3) DISCOLORATION PREVENTING AGENT | NONE |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 11

EXAMPLE 4

| (1) PIGMENT (DYE) | TH-107 : 0.5 |
|---|---|
| (2) COLORING ASSISTANT | TETRAMETHYLTHIURAM MONOSULFIDE : 2.5 |
| (3) DISCOLORATION PREVENTING AGENT | NONE |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 12

EXAMPLE 5

| (1) PIGMENT (DYE) | TH-107 : 0.5 |
|---|---|
| (2) COLORING ASSISTANT | TETRAETHYLTHIURAM DISULFIDE : 2.5 |
| (3) DISCOLORATION PREVENTING AGENT | NONE |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 13

EXAMPLE 6

| (1) PIGMENT (DYE) | TH-107 : 0.5 |
|---|---|
| (2) COLORING ASSISTANT | 2-BENZOTHIAZOLYL DIETHYLDITHIOCARBAMATE : 2.5 |
| (3) DISCOLORATION PREVENTING AGENT | NONE |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 14

EXAMPLE 7

| (1) PIGMENT (DYE) | PSD-HR : 0.5 |
|---|---|
| (2) COLORING ASSISTANT | TETRAMETHYLTHIURAM MONOSULFIDE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 15

EXAMPLE 8

| (1) PIGMENT (DYE) | PSD-HR : 0.5 |
|---|---|
| (2) COLORING ASSISTANT | TETRAETHYLTHIURAM DISULFIDE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 16

EXAMPLE 9

| (1) PIGMENT (DYE) | PSD-HR : 0.5 |
|---|---|
| (2) COLORING ASSISTANT | 2-BENZOTHIAZOLYL DIETHYLDITHIOCARBAMATE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 17

EXAMPLE 10

| (1) PIGMENT (DYE) | TH-107 : 0.5 |
|---|---|
| (2) COLORING ASSISTANT | TETRAMETHYLTHIURAM MONOSULFIDE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 18

EXAMPLE 11

| (1) PIGMENT (DYE) | TH-107 : 0.5 |
|---|---|
| (2) COLORING ASSISTANT | TETRAETHYLTHIURAM DISULFIDE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 19

EXAMPLE 12

| (1) PIGMENT (DYE) | TH-107 : 0.5 |
|---|---|
| (2) COLORING ASSISTANT | 2-BENZOTHIAZOLYL DIETHYLDITHIOCARBAMATE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 20

EXAMPLE 13

| (1) PIGMENT (DYE) | NC-BLUE-5 : 0.2 |
|---|---|
| (2) COLORING ASSISTANT | 2-MERCAPTOBENZOTHIAZOLE : 2 |
| (3) DISCOLORATION PREVENTING AGENT | NONE |
| (4) BINDER | ETHYL CELLULOSE : 12.5 |
| (5) SOLVENT | METHYL ETHYL KETONE : ABOUT 85 |

FIG. 21

EXAMPLE 14

| (1) PIGMENT (DYE) | NC-BLUE-5 : 0.2 |
|---|---|
| (2) COLORING ASSISTANT | 2-MERCAPTOBENZOTHIAZOLE : 2 |
| (3) DISCOLORATION PREVENTING AGENT | 4,4'-(1-α-METHYLBENZYLIDENE)BISPHENOL : 3.0 |
| (4) BINDER | ETHYL CELLULOSE : 12.5 |
| (5) SOLVENT | METHYL ETHYL KETONE : ABOUT 85 |

FIG. 22

EXAMPLE 15

| (1) PIGMENT (DYE) | PSD-3G : 0.5 |
|---|---|
| (2) COLORING ASSISTANT | 2-AMINO-5-MERCAPTO-1,3,4-THIADIAZOLE : 0.4 |
| (3) DISCOLORATION PREVENTING AGENT | NONE |
| (4) BINDER | VINYL BUTYRAL : 12.5 |
| (5) SOLVENT | METHYL ETHYL KETONE : ABOUT 85 |

FIG. 23

EXAMPLE 16

| (1) PIGMENT (DYE) | TH-107 : 0.5 |
|---|---|
| (2) COLORING ASSISTANT | TETRAETHYLTHIURAM DISULFIDE : 1.6 |
| (3) DISCOLORATION PREVENTING AGENT | 1,1-BIS(4-HYDROXYPHENYL)CYCLOHEXANE : 4 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 24

EXAMPLE 17

| (1) PIGMENT (DYE) | TH-107 : 0.5 |
|---|---|
| (2) COLORING ASSISTANT | TETRA-n-BUTYLTHIURAM DISULFIDE : 1.6 |
| (3) DISCOLORATION PREVENTING AGENT | 1,1-BIS(4-HYDROXYPHENYL)CYCLOHEXANE : 4 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 25

EXAMPLE 18

| (1) PIGMENT (DYE) | TH-107 : 0.5 |
|---|---|
| (2) COLORING ASSISTANT | 2-BENZOTHIAZOLYL DIETHYLDITHIOCARBAMATE : 1.6 |
| (3) DISCOLORATION PREVENTING AGENT | 1,1-BIS(4-HYDROXYPHENYL)CYCLOHEXANE : 4 |
| (4) BINDER | ETHYL CELLULOSE : 12.5 |
| (5) SOLVENT | MIXTURE OF METHYL ETHYL KETONE AND TOLUENE (9:1) : ABOUT 85 |

FIG. 26

EXAMPLE 19

| (1) PIGMENT (DYE) | NC-BLUE-5 : 0.2<br>+ PARAROSANILINE : 0.05 |
|---|---|
| (2) COLORING ASSISTANT | TETRAETHYLTHIURAM DISULFIDE : 2.5 |
| (3) DISCOLORATION PREVENTING AGENT | NONE |
| (4) BINDER | ETHYL CELLULOSE : 12.5 |
| (5) SOLVENT | METHYL ETHYL KETONE : ABOUT 85 |

FIG. 27

EXAMPLE 20

| (1) PIGMENT (DYE) | NC-BLUE-5 : 0.2 |
| --- | --- |
| | + PARAROSANILINE : 0.05 |
| (2) COLORING ASSISTANT | TETRAETHYLTHIURAM DISULFIDE : 2.5 |
| (3) DISCOLORATION PREVENTING AGENT | 4,4'-(1-α-METHYLBENZYLIDENE)BISPHENOL : 5 |
| (4) BINDER | ETHYL CELLULOSE : 12.5 |
| (5) SOLVENT | METHYL ETHYL KETONE : ABOUT 85 |

FIG. 28

EXAMPLE 21

| (1) PIGMENT (DYE) | PSD-HR : 0.5 |
| --- | --- |
| | + VICTORIA BLUE : 0.05 |
| (2) COLORING ASSISTANT | TETRAETHYLTHIURAM DISULFIDE : 2.5 |
| (3) DISCOLORATION PREVENTING AGENT | NONE |
| (4) BINDER | ETHYL CELLULOSE : 12.5 |
| (5) SOLVENT | METHYL ETHYL KETONE : ABOUT 85 |

EXAMPLE 22

| (1) PIGMENT (DYE) | PSD-HR : 0.5<br>+ VICTORIA BLUE : 0.05 |
| --- | --- |
| (2) COLORING ASSISTANT | TETRAETHYLTHIURAM DISULFIDE : 2.5 |
| (3) DISCOLORATION PREVENTING AGENT | 1,1-BIS(4-HYDROXYPHENYL)CYCLOHEXANE : 5 |
| (4) BINDER | ETHYL CELLULOSE : 12.5 |
| (5) SOLVENT | METHYL ETHYL KETONE : ABOUT 85 |

(CHEMICAL FORMULA 1)

FIG. 31

—SH (CHEMICAL FORMULA 2)

INDICATOR FOR PLASMA STERILIZATION

TECHNICAL FIELD

The present invention relates to an indicator for plasma sterilization that is used to determine whether instruments and other products to be sterilized have experienced a sterilization treatment process, or to confirm whether sterilization has been efficiently performed, by the color tone change of the indicator, when sterilizing medical instruments and other products and the like by a hydrogen peroxide low temperature plasma sterilizing method.

BACKGROUND ART

Conventionally, (1) a high pressure vapor sterilization method or (2) an ethylene oxide sterilization method has been used in order to sterilize instruments used for surgical procedures or remedial treatments in medical institutions such as hospitals and the like.

In these high pressure vapor sterilization method and ethylene oxide sterilization method, it is extremely important (1) to determine whether instruments and other products to be sterilized have experienced a sterilization treatment process or (2) to detect whether sterilizing conditions applied to instruments are appropriate.

In a method of the determination method or the detecting method, a chemical indicator for sterilization whose color tone is changed by sterilization has been used, however, as the indicator for sterilization, a dedicated indicator for each sterilization method should be used.

However, the high pressure vapor sterilization method which has been conventionally used can be applied to only instruments which are resistant to high temperature and high pressure. On the other hand, the ethylene oxide gas sterilization method can be performed under relatively low temperature (40 to 60° C.) so that this method is often employed for sterilization of an endoscope, a plastic instrument which is heat-sensitive or the like. However, since strongly poisonous ethylene oxide is adsorbed onto the instruments after sterilization so as to tend to remain, this method has the disadvantage of requiring removal of the ethylene oxide which has adhered to the instruments after sterilization.

Recently, as a sterilization method which can replace the high pressure vapor sterilization method or the ethylene oxide sterilization method, a plasma sterilization method utilizing bactericidal ability of low temperature gas plasma with an oxidative gas such as hydrogen peroxide and the like or other gases has been used.

According to the sterilization process of the plasma sterilization method using "STERRAD 100" (trademark) which is one of presently commercially available typical hydrogen peroxide low temperature plasma sterilizers developed by Johnson & Johnson Medical (the United States), instruments to be sterilized are loaded into the inside of the sterilizer, and the inside of the sterilizer is highly evacuated, and then, a fixed amount of a hydrogen peroxide solution is injected and vaporized, the step of diffusing the vaporized hydrogen peroxide gas thoroughly over the inside of the strilizer (diffusion step, about 50 min) and the subsequent step of generating a plasma from the hydrogen peroxide gas by applying a high frequency voltage (plasma generation step, about 15 min) are provided.

In this plasma generation step, a plasma is generated from the hydrogen peroxide gas so as to contain many free radicals such as highly reactive .O radicals, .OH radicals or .OOH radicals, thereby providing an noticeable improvement in an sterilization effect compared to sterilization performed merely in hydrogen peroxide (for example, U.S. Pat. No. 4,169,123), and as a result thereof, sterilization can be performed at a temperature as low as about 45° C., and beside, can be realized for a short'time as mentioned above.

After the plasma generation step, when stopping applying high frequency energy, the plasma state ceases instantaneously so that highly reactive free radicals and the like recombine to form oxygen and water thereby allowing hazardous substances not to remain.

The applicant of the present application has already proposed a chemical indicator used for such a new low temperature gas plasma sterilization method using hydrogen peroxide (refer to the specification of Japanese Patent Application No. H 9-365688 or Japanese Patent Application Laid-Open No. H 11-178904 or the like).

The technical content of the above mentioned application by the applicant of the present application is based on the principle that "an indicator including a basic pigment such as triphenylmethanes and the like and a certain color change assistant is discolored colorless by oxidizing power of a plasma formed from hydrogen peroxide or a hydrogen peroxide vapor."

It is an object of the present invention to provide an indicator wherein, contrary to the indicator of the above mentioned application, colorless pigments as used in pressure-sensitive copying papers or thermosensitive recording papers are used so that the indicator is clearly colored by the action of a plasma from hydrogen peroxide or a hydrogen peroxide vapor and has good stability in storage.

SUMMARY OF THE INVENTION

It is an object of an indicator for plasma sterilization of the present invention to provide an indicator for plasma sterilization which comprises a colorless chromogenic pigment, a coloring assistant and a binder (a binding agent), wherein the color tone change of the indicator occurs by a hydrogen peroxide low temperature sterilization method.

Conventionally, it has been known that leucocrystal violet (a structural formula shown in FIG. 1) obtained by reduction of crystal violet which is a triphenylmethane pigment is easy to color by oxidation.

However, leucocrystal violet has neither good stability in air nor good stability to light so that an ink including leucocrystal violet which is applied onto a base material has a strong tendency to be colored by oxidation of the pigment during storage in air.

Moreover, with regard to a triphenylmethane lactone type colorless dye (triphenylmethane phthalide) as presently used in pressure-sensitive copying papers or thermosensitive recording papers which has one lactone ring in a molecule of a triphenylmethane compound, for example Crystal Violet lactone (CVL, a structural formula shown in FIG. 2) is much stabler than the leucocrystal violet as mentioned above and has good stability in air, however, an ink including such a pigment which is applied onto a base material is hardly colored when subjected to a hydrogen peroxide low temperature plasma sterilization treatment.

Hence, using colorless pigments such as; Crystal Violet lactone (a structural formula shown in FIG. 2) which is a typical example of triphenylmethane phthalide as presently used for manufacturing pressure-sensitive copying papers or thermosensitive recording papers; a phthalide (a structural formula shown in FIG. 3) in which one benzene ring of triphenylmethane phthalide is substituted with an indole ring; a phthalide (a structural formula shown in FIG. 4) with a structure in which another benzene ring of the phthalide is further substituted with a pyridine ring; a phthalide (a structural formula shown in FIG. 5) with a fluorene structure in which two benzene rings of triphenylmethane phthalide are combined to form a closed ring; and fluoran compounds (structural formulae shown in FIG. 6 and FIG. 7) in which two benzene rings of triphenylmethane phthalide are combined with an oxygen atom to form a closed ring, inks are prepared from such pigments into which various types of additives and binders (binding agents) are added, and with regard to samples wherein the inks are applied to base materials, color change property by a hydrogen peroxide low temperature plasma sterilization has been investigated.

As a result of this test, it was found that only samples using colorless fluoran pigments in combination with compounds having a dithiocarbamyl group (a chemical formula shown in FIG. 30) or a mercapto group (a chemical formula shown in FIG. 31) were clearly colored by a hydrogen peroxide low temperature plasma sterilization.

As a result of additional study of coloring in a hydrogen peroxide vapor with regard to the above-mentioned samples, there occurs coloring in the samples using colorless pigments other than colorless fluoran pigments, which are mixed with compounds having a dithiocarbamyl group (FIG. 30) or a mercapto group (FIG. 31) as additives, during the process of hydrogen peroxide low temperature plasma sterilization, however, the colored pigments are oxidized and discolored, and as a result thereof, the coloring density is not improved. In contrast to this, it turned out that the samples using colorless fluoran pigments are clearly colored at high density because the colored pigments are extremely difficult to be oxidized during the process of hydrogen peroxide low temperature plasma sterilization.

In addition, with regard to colorless fluoran pigments, pigments with a chemical structure other than the two types as mentioned above are combined with compounds having a dithiocarbamyl group or compounds having a mercapto group which are two systems of coloring assistants so as to prepare indicators, on which hydrogen peroxide low temperature plasma sterilization process tests are conducted so that it was confirmed that clear coloration occurs in all the indicators.

As for an indicator wherein an ink including a colorless fluoran pigment and a compound having a dithiocarbamyl group or mercapto group as an additive (a coloring assistant) is applied to a base material, a color tone of the indicator is almost colorless before sterilization. The indicator also has a stable coloration property during a hydrogen peroxide low temperature plasma sterilization process and finally reaches a constant color tone and color density.

Furthermore, it was recognized that stability (discoloration property) of color (color density) of an indicator at high humidity after sterilization treatment is related to:

(1) the type of an individual colorless fluoran pigment;
(2) the type and the mixing amount of a compound having a dithiocarbamyl group or a compound having a mercapto group (coloring assistants); and
(3) the type of a binder and so on.

With regard to the indicators of the present invention, mixing of polyphenol compounds with the indicators is effective in improving or further enhancing stability of a color tone or color density of the indicators at high humidity after sterilization treatment as mentioned above.

Since a large mixing amount of polyphenol compounds generally allows some parts of colorless fluoran pigments in indicators to be colored so as to cause "coloration fogging" in a color tone of the indicators, the mixing amount of polyphenol compounds should be in the range wherein the color tone of the indicators, to be colored, prior to sterilization is not significantly affected by the mixing amount.

Moreover, as another effect of mixing of polyphenol compounds when mixing the polyphenol compounds, the coloration of indicators during hydrogen peroxide low temperature plasma sterilization is frequently promoted. However, when mixing only polyphenol compounds, such effect is hardly observed, whereas the effect of promoting the coloration is recognized only when mixing polyphenol compounds in combination with compounds having a mercapto group or compounds having a dithiocarbamyl group which are coloring assistants.

Furthermore, with regard to stability in storage of indicators prior to performing sterilization, it is important that coloration or color change by environmental light such as sunlight, fluorescent light or the like is small, whereas with regard to the indicators of the present invention comprising a colorless fluoran pigment, compounds having a mercapto group or compounds having a dithiocarbamyl group as coloring assistants and a binder, it was found the types of the colorless fluoran pigments to be used and the types and the mixing amounts of the coloring assistants are the most influential factors.

Since a larger mixing amount of coloring assistants generally allows coloration of indicators by light to increase, it is preferable that the mixing amount be small. Moreover, comparing coloration by light of an indicator mixed with a compound having a dithiocarbamil group as a coloring assistant to that of an indicator mixed with a compound having a mercapto group, the former's coloration is less than the latter's coloration and the former is preferable.

BRIEF DESCRIPTION OF THE DRAWINGS

FIG. 9 is a table showing Example 2 of an indicator for plasma sterilization according to the present invention;
FIG. 10 is a table showing Example 3 of an indicator for plasma sterilization according to the present invention;
FIG. 11 is a table showing Example 4 of an indicator for plasma sterilization according to the present invention;
FIG. 12 is a table showing Example 5 of an indicator for plasma sterilization according to the present invention;
FIG. 13 is a table showing Example 6 of an indicator for plasma sterilization according to the present invention;
FIG. 14 is a table showing Example 7 of an indicator for plasma sterilization according to the present invention;
FIG. 15 is a table showing Example 8 of an indicator for plasma sterilization according to the present invention;
FIG. 16 is a table showing Example 9 of an indicator for plasma sterilization according to the present invention;

FIG. 17 is a table showing Example 10 of an indicator for plasma sterilization according to the present invention;

FIG. 18 is a table showing Example 11 of an indicator for plasma sterilization according to the present invention;

FIG. 19 is a table showing Example 12 of an indicator for plasma sterilization according to the present invention;

FIG. 20 is a table showing Example 13 of an indicator for plasma sterilization according to the present invention;

FIG. 21 is a table showing Example 14 of an indicator for plasma sterilization according to the present invention;

FIG. 22 is a table showing Example 15 of an indicator for plasma sterilization according to the present invention;

FIG. 23 is a table showing Example 16 of an indicator for plasma sterilization according to the present invention;

FIG. 24 is a table showing Example 17 of an indicator for plasma sterilization according to the present invention;

FIG. 25 is a table showing Example 18 of an indicator for plasma sterilization according to the present invention;

FIG. 26 is a table showing Example 19 of an indicator for plasma sterilization according to the present invention;

FIG. 27 is a table showing Example 20 of an indicator for plasma sterilization according to the present invention;

FIG. 28 is a table showing Example 21 of an indicator for plasma sterilization according to the present invention;

FIG. 31 illustrates a chemical formula of mercapto group.

DESCRIPTION OF THE PREFERRED EMBODIMENTS

Figure 1:
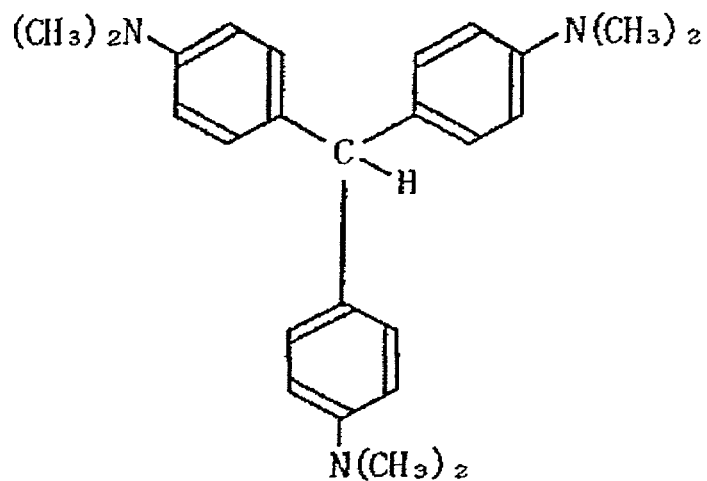
FIG. 1 illustrates a structural formula of leucocrystal violet which is a pigment.

Now, an indicator for plasma sterilization according to the present invention will be described in detail based on the accompanying drawings.

The present invention is an indicator for plasma sterilization wherein an ink, including (a) a colorless fluoran pigment, (b) a compound having a dithiocarbamyl group (a coloring assistant) or a compound having a mercapto group (a coloring assistant) and (c) a binder (a binding agent), and (d) a polyphenol compound for the purpose of preventing discoloration of the indicator in highly humid surroundings after sterilization treatment, when necessary, is printed on or applied to a base material.

The colorless fluoran pigment which is mixed in the above mentioned indicator for plasma sterilization changes color (is colored) into a color tone typical of the pigment by hydrogen peroxide low temperature sterilization.

Additionally, it was recognized that the speed of color change (coloration) of the indicator during sterilization treatment is related to:

(1) the type of an individual pigment;
(2) the type and the mixing amount of a compound having a dithiocarbamyl group or a compound having a mercapto group (coloring assistants);
(3) the type of a binder; and
(4) the type and the mixing amount of a polyphenol compound which is mixed when necessary.

In general, indicators for sterilization are classified roughly into two types: process indicators and indicators for detecting sterilization effects. The former process indicators are applied to or printed on conspicuous areas of the surface of packaging materials for sterilization so as to determine whether objects to be sterilized have experienced a sterilization process (being used as signs in order to avoid confusion between articles having been sterilized and yet-to-be sterilized articles), while the latter indicators for detecting sterilization effects are used for determining whether sterilization effects applied to objects are appropriate (whether sterilizing conditions sufficient for microorganisms to be extinct are obtained or not) on the basis of the degree of color tone change of the indicators, which have been printed on cards and the like, being sterilized along with objects to be sterilized.

Thus, as for the process indicators, indicators which cause a clear color difference (a color tone change or a change of color density) between before and after sterilization treatment process, is sufficient for the process indicators, while, with regard to the indicators for detecting sterilization effects, there is a necessity to be able to determine sterilization effects (which is gradually enhanced during the sterilization process) based on color tone or color density.

In hydrogen peroxide low temperature plasma sterilization, there are generally a diffusion step of diffusing a hydrogen peroxide vapor and a subsequent plasma generation step. However, it is in the plasma generation step that all microorganisms which adhere to objects to be sterilized become extinct, and therefore, the indicators for detecting sterilization effects is required to have little color change (coloration) during the diffusion step of diffusing a hydrogen peroxide vapor, and is required to change color into a final color tone or color density during the plasma generation step.

Incidentally, in the case of the indicator for plasma sterilization of the present invention, as described above, it has been recognized that the speed of coloration during sterilization treatment is related to:

(1) the type of an individual colorless fluoran pigment;
(2) the type and the mixing amount of a compound having a dithiocarbamyl group (a coloring assistant) or a compound having a mercapto group (a coloring assistant);
(3) the type of a binder; and
(4) the type and the mixing amount of a polyphenol compound which is mixed when necessary.

Among the above factors, the type and the mixing amount of a compound having a dithiocarbamyl group or a compound having a mercapto group as a coloring assistant have a noticeable effect on the speed of coloration during sterilization. It was found that among coloring assistants, compounds having a mercapto group generally have a strong coloration promoting property in a hydrogen peroxide vapor, and also have a high coloration promoting property in a hydrogen peroxide vapor, for example, in tests at about room temperature.

Additionally, it was found that the compounds having a dithiocarbamyl group have the property of promoting coloration in a hydrogen peroxide vapor which varies depending on the types of the compounds having a dithiocarbamyl group and that some compounds having a dithiocarbamyl group are as high in the property as the compounds having a mercapto group and other compounds having a dithiocarbamyl group are lower in the property than the compounds having a mercapto group.

When preparing indicators for detecting sterilization effects, as mentioned above, since little coloration is preferred to proceed in the diffusion step of diffusing a hydrogen peroxide vapor in hydrogen peroxide low temperature plasma sterilization, it is effective to select, as a coloring assistant from compounds having a dithiocarbamyl group, an compound which has a low coloration promoting property in a hydrogen peroxide vapor and then to mix an appropriate amount of the selected compound.

Besides the above-mentioned colorless fluoran pigment as an essential ingredient, it is possible to mix another pigment which does not change color by hydrogen peroxide low temperature plasma sterilization, into the indicator of the present invention, so as to modify a color tone before sterilization and after sterilization.

Moreover, for the indicators for plasma sterilization of the present invention, it is possible to mix a pigment which is discolored (loses color) by hydrogen peroxide low temperature plasma sterilization in the presence of compounds having a dithiocarbamyl group or a mercapto group, as a pigment other than the colorless fluoran pigment being an essential ingredient, so as to allow the color tone of the indicator before the sterilization not to be colorless but to be colored.

As a pigment mixed into an indicator for plasma sterilization of the present invention that is discolored (loses color) during sterilization treatment, for example, cyanine basic pigments or triphenylmethane basic pigments as described in the above-mentioned Japanese Patent Application Laid-Open No. H 11-178904 filed by the applicant of the present invention can be used.

In this case, if a pigment the color of which is significantly different from a color tone of a colorless fluoran pigment as an essential ingredient after sterilization treatment is used as a pigment which loses color during sterilization treatment, an indicator which has a wide range of a color change (has a large color difference) between before and after sterilization can be prepared.

A pigment as an ingredient necessary to prepare an indicator for plasma sterilization of the present invention is a pigment which is colored during a hydrogen peroxide low temperature plasma sterilization step, and a colorless fluoran pigment is used as the pigment.

Examples of the colorless fluoran pigment include 3,6-dimethoxyfluoran, 3-diethylamino-7-chlorofluoran, 3-diethylamino-benzo[a]fluoran, 4-amino-8-diethylamino-benzo(a)fluoran, 4-benzylamino-8-diethylamino-benzo[a]fluoran, 2-amino-8-diethylamino-benzo[a]fluoran, 2-mesidino-8-diethylamino-benzo[c]fluoran, 3-(N,N-diethylamino)-7-(N,N-dibenzylamino)fluoran, 3-diethylamino-7-alkyl(C8)aminofluoran, 2-(N-methyl-N-phenylamino)-6-(N-p-tolyl-N-ethylamino)fluoran, 3-pyrrolidino-7-(N,N-dibenzylamino)fluoran, 3-pyrrolidino-7-cyclohexylaminofluoran, 3-diethylamino-7-cyclohexylaminofluoran, 3-diethylamino-7-cyclohexyl-N-benzylaminofluoran, 2-anilino-3-methyl-6-diethylaminofluoran, 2-anilino-3-methyl-6-(N-ethyl-p-toluidino)fluoran, 2-p-toluidino-3-methyl-6-(N-ethyl-p-toluidino)fluoran, 3-(N-cyclohexyl-N-methylamino)-6-methyl-7-anilinofluoran, 3-dibutylamino-7-(o-chloroanilino)fluoran, 3-dibutylamino-7-fluoroanilinofluoran, 3-diethylamino-6-chloroanilinofluoran, and the like.

Figures 29, 30:
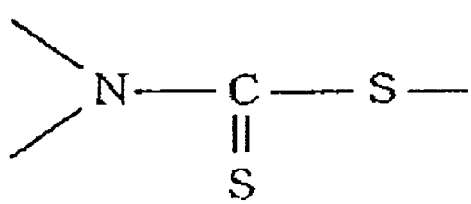
FIG. 29 is a table showing Example 22 of an indicator for plasma sterilization according to the present invention.
FIG. 30 illustrates a chemical formula of dithiocarbamyl group.
Figure 31:
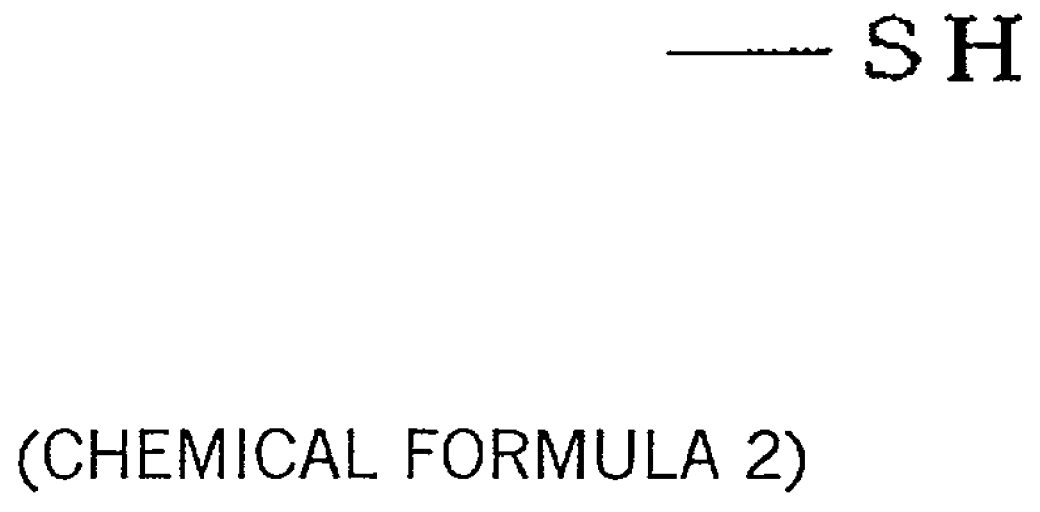

A coloring assistant as an ingredient being essential to preparing an indicator for plasma sterilization of the present invention is a compound having a dithiocarbamyl group (FIG. 30) or a compound having a mercapto group (FIG. 31).

Examples of the above-mentioned compounds (coloring assistants) having a dithiocarbamyl group (FIG. 30) include tetramethylthiuram monosulfide, tetramethylthiuram disulfide, tetraethylthiuram disulfide, tetra-n-butylthiuram disulfide, N,N'-dimethyl-N,N'-diphenylthiuram disulfide, dipentamethylenethiuram monosulfide, dipentamethylenethiuram disulfide, dipentamethylenethiuram tetrasulfide, p-xylylene bis(N,N-diethyldithiocarbamate), 2-benzothiazolyl diethyldithiocarbamate, 4-dimethylaminobenzylideneRhodamine and the like.

Examples of the compounds having a dithiocarbamyl group (FIG. 30) used as a coloring assistant in the indicator for plasma sterilization of the present invention, that provide the indicator which is slowly colored in a hydrogen peroxide vapor and is completely colored by a hydrogen peroxide low temperature plasma sterilization treatment, include tetra-n-butylthiuram disulfide and 2-benzothiazolyl diethyldithiocarbamate.

Furthermore, examples of the compounds (coloring assistants) having a mercapto group (FIG. 31) include 2-mercaptobenzothiazole, 2-mercaptobenzoimidazole, 2-mercaptobenzoxazole, 3-mercapto-1,2,4-triazole, 3-mercapto-4-methyl-4H-1,2,4-triazole, 2-mercaptothiazoline, 5-methyl-1,3,4-thiadiazole-2-thiol, 1-phenyl-5-mercapto-1H-tetrazole, 2-amino-5-mercapto-1,3,4-thiadiazole, 2,5-dimercapto-1,3,4-thiadiazole, 5-mercapto-1-methyltetrazole, mercaptosuccinic acid and the like.

For a binder (a binding agent) as an ingredient being essential to preparing an indicator for plasma sterilization of the present invention, it is necessary to select a binder which not only dissolves well in a solvent used for dissolving a coloring assistant, a colorless pigment and the like that are mixing ingredients of an ink, but also is well compatible with the above-mentioned pigment, coloring assistant and the like, in order to enhance stability in long term storage and clearness of color tone of the indicator.

There are no special restrictions to examples of materials capable of being used as a binder (a binding agent), and the examples mainly include cellulose derivatives such as cellulose acetate, cellulose butyrate, cellulose nitrate, ethyl cellulose, hydroxypropyl cellulose and the like, vinyl polymers such as poly(vinyl acetate), a vinyl acetate/vinyl pyrrolidone copolymer, poly(vinyl butyral), a styrene/acrylonitrile copolymer and the like.

Examples of polyphenol compounds which are not ingredients being essential to preparing an indicator for plasma sterilization of the present invention, but, in many instances, ingredients being effective in preventing discoloration of the indicator in highly humid surroundings after sterilization treatment and in further enhancing coloring density of the indicator during sterilization treatment process, include diphenol acid, phenolphthalein, bis(4-hydroxyphenyl)propane, 1,1-bis(4-hydroxyphenyl)cyclohexane, bis(4-hydroxyphenyl)sulfone, bis(4-hydroxyphenyl)sulfide, 9,9-bis(4-hydroxyphenyl)fluorene, 4,4'-(1-α-methylbenzylidene)bisphenol, α, α'-bis(4-hydroxyphenyl)-1,4-diisopropylbenzene, 4,4'-bisbutylidenebis(3-methyl-6-tertbutylphenol), α,α,α'-tris(4-hydroxyphenyl)-1-ethyl-4-isopropylbenzene, oligomers of 4-phenylphenol and formaldehyde, polyvinylphenol [poly(p-hydroxystyrene)] and the like.

Mixing amounts of a colorless pigment, a coloring assistant, a binder (a binding agent) and a solvent as essential ingredients for mixing to form an ink in order to prepare an indicator for plasma sterilization of the present invention are not necessarily within the following range because the amounts vary depending on the types and properties of the respective ingredients, however, the mixing amounts are approximately in the order of the following:

(1) a colorless pigment: 0.1 to 1 part;
(2) a coloring assistant: 0.5 to 6 parts;
(3) a binder: 10 to 30 parts; and
(4) a solvent: 70 to 85 parts.

Figure 6:
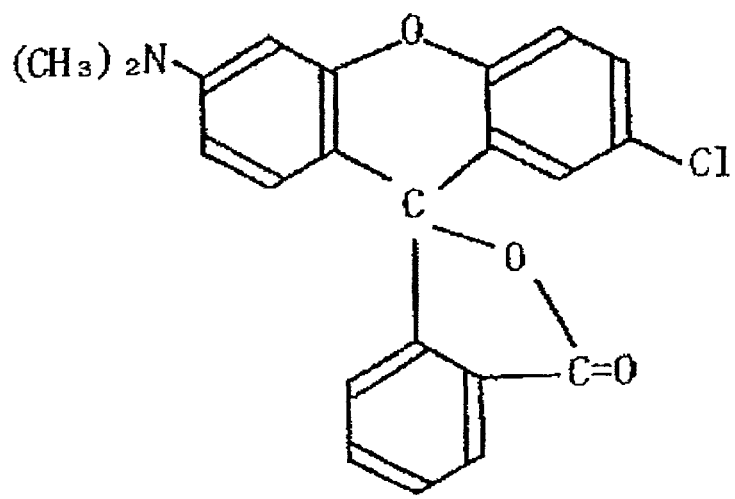
FIG. 6 illustrates a structural formula of PSD-HR which is a pigment.
Figures 7, 8:
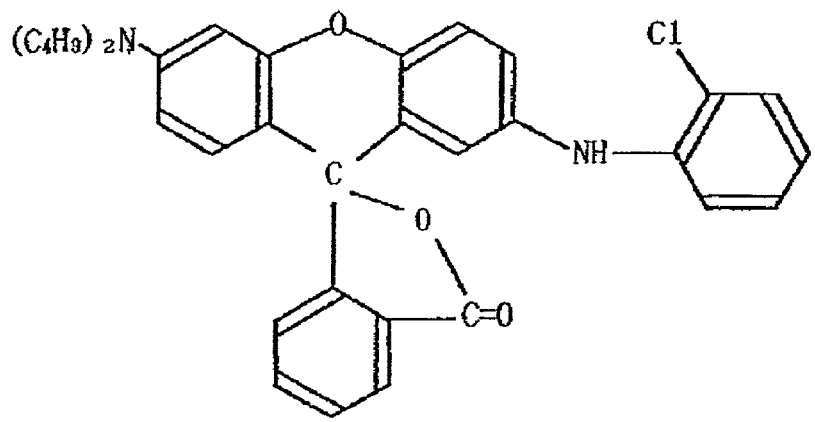
FIG. 7 illustrates a structural formula of TH-107 which is a pigment.
FIG. 8 is a table showing Example 1 of an indicator for plasma sterilization according to the present invention.

Using the following agents:

(1) as a pigment, 0.5 parts by weight of PSD-HR (produced by Nippon Soda, FIG. 6) which is a colorless fluoran pigment;

(2) as a coloring assistant, 2.5 parts by weight of tetramethylthiuram monosulfide in Example 1, 2.5 parts by weight of tetraethylthiuram disulfide in Example 2, and 2.5 parts by weight of 2-benzothiazolyl diethyldithiocarbamate in Example 3;

(3) as a binder (a binding agent), 12.5 parts by weight of ethyl cellulose (Ethocell No. 4 produced by Dow Chemical); and (4) as a solvent, about 85 parts by weight of a mixture of methyl ethyl ketone and toluene (9:1), inks were prepared, and then, each of the inks was applied onto a base material made of polyethylene synthetic paper (Tyvek produced by Du Pont) with a 0.25 m/m wire bar by hand, and indicators for plasma sterilization of Example 1 (FIG. 8), Example 2 (FIG. 9) and Example 3 (FIG. 10) were prepared.

These indicators were colorless respectively, and when subjected to sterilization treatment with a plasma sterilizer (STERRAD 100) manufactured by Johnson & Johnson Medical in the United States under the standard condition (under the condition of a certain number of instruments being loaded in the sterilizer), the indicators changed color in red (were colored red).

In addition, in order to investigate whether there is discoloration of the indicators or not, which were subjected to sterilization treatment at high humidity or not, tests were performed wherein the samples after sterilization are left in a constant temperature and constant humidity bath at a temperature of 40° C. and at a humidity of 90% RH for 1 week, however, no discoloration was observed.

In order to perform a comparison with the above-mentioned Example 1 (FIG. 8), Example 2 (FIG. 9) and Example 3 (FIG. 10), inks having the ingredients used in the above-mentioned Examples except that the coloring assistants are not mixed were prepared (Comparative Examples 1 to 3), and then, each of the inks was applied onto Tyvek by hand, and indicators for plasma sterilization were prepared.

When these were subjected to sterilization treatment with the plasma sterilizer manufactured by Johnson & Johnson Medical as in the case of the above-mentioned Examples 1 to 3, the samples of Comparative Examples did not change color (were not colored) at all.

Inks were prepared in a manner similar to that of the above-mentioned Example 1 to Example 3 except that as a pigment, 0.5 parts by weight of TH-107 (produced by Hodogaya Chemical Industry, FIG. 7) which is a colorless fluoran pigment was used, and then, each of the inks was applied onto Tyvek produced by Du Pont, with a 0.25 m/m wire bar by hand, and indicators for plasma sterilization of Example 4 (FIG. 11), Example 5 (FIG. 12) and Example 6 (FIG. 13) were prepared.

Each of the indicators for plasma sterilization of the above-mentioned Example 4 (FIG. 11), Example 5 (FIG. 12) and Example 6 (FIG. 13) was colorless, and when subjected to sterilization treatment in a manner similar to that of the above-mentioned Example 1 (FIG. 8), Example 2 (FIG. 9) and Example 3 (FIG. 10) with the plasma sterilizer manufactured by Johnson & Johnson Medical under the standard condition, each of the indicators changed color in black (were colored black).

In order to investigate whether there is a discoloration property of the indicators or not, which were subjected to sterilization treatment in highly humid surroundings or not, tests were performed wherein the samples after sterilization are left in a constant temperature and constant humidity bath at a temperature of 40° C. and at a humidity of 90% RH for 1 week, however, no discoloration was observed.

Inks having compositions similar to those in the above-mentioned Example 4 (FIG. 11), Example 5 (FIG. 12) and Example 6 (FIG. 13) except that the coloring assistants are not mixed were prepared, and then these inks were applied onto Tyvek by hand, and indicators for plasma sterilization of Comparative Example 4 to Comparative Example 6 were prepared. When these were subjected to sterilization treatment under the same condition as in the above-mentioned Example 4 to Example 6 with the plasma sterilizer manufactured by Johnson & Johnson Medical, the samples of Comparative Examples were hardly colored.

Inks having the compositions of the above-mentioned Example 1 to Example 6 and further being mixed with 5 parts by weight of 1,1-bis(4-hydroxyphenyl)cyclohexane as a polyphenol compound which has a discoloration preventing effect in highly humid surroundings after sterilization and a coloration promoting effect during plasma sterilization were prepared respectively, and then these inks were applied onto Tyvek by hand, and indicators for plasma sterilization of Example 7 (FIG. 14), Example 8 (FIG. 15), Example 9 (FIG. 16), Example 10 (FIG. 17), Example 11 (FIG. 18), and Example 12 (FIG. 19) were prepared.

The indicators of Example 7 to Example 12 were slightly of color respectively because the colorless pigments of them were only partly colored due to mixing of 1,1-bis(4-hydroxyphenyl)cyclohexane that is a polyphenol compound, and when these were subjected to sterilization treatment under the same condition as in Example 1 to Example 6 with the plasma sterilizer manufactured by Johnson & Johnson Medical, the samples of Comparative Examples changed color somewhat deeper than the samples of Example 1 to Example 6 respectively.

When tests were performed wherein these samples after sterilization are left in a constant temperature and constant humidity bath at a temperature of 40° C. and at a humidity of 90% RH for 1 week, no discoloration was observed.

In order to investigate a coloration property during sterilization treatment of indicators which are not mixed with a coloring assistant but only with 1,1-bis(4-hydroxyphenyl)cyclohexane as mentioned above, inks having compositions similar to those in Examples 7 to 12 except that the coloring assistants are not mixed were prepared, and then these inks were applied onto Tyvek by hand, and indicators for plasma sterilization of Comparative Example 7 to Comparative Example 12 were prepared.

The samples of Comparative Examples 7 to 12 were not completely colorless respectively because in coloration fogging in them was only slightly caused due to mixing of 1,1-bis(4-hydroxyphenyl)cyclohexane which is a polyphenol compound, and when these were subjected to sterilization treatment under the same condition as Examples 7 to 12 with the plasma sterilizer manufactured by Johnson & Johnson Medical, the samples of Comparative Examples were just slightly colored.

Using the following agents, as a pigment, 0.2 parts by weight of NC-Blue-5 (produced by Hodogaya Chemical Industry) which is a colorless fluoran pigment; as a coloring assistant, 2.0 parts by weight of 2-mercaptobenzothiazole; as a binder, 12.5 parts by weight of ethyl cellulose (Ethocell No. 4 produced by Dow Chemical); and as a solvent, about 85 parts by weight of methyl ethyl ketone, an ink was prepared, and then, the ink was applied onto a base material made of polypropylene synthetic paper (Oji-Yuka Synthetic Paper, YUPO) with a 0.25 m/m wire bar by hand, and an indicator for plasma sterilization of Example 13 (FIG. 20) was prepared.

This indicator was almost colorless, and when this indicator was subjected to sterilization treatment as in the case of Examples 1 to 12 with STERRAD 100 manufactured by Johnson & Johnson Medical under the standard condition, the sample changed color in blue (was colored blue).

When a test was performed wherein the sample of this indicator after sterilization treatment is left in a constant temperature and constant humidity bath at a temperature of 40° C. and at a humidity of 90% RH for 1 week, color density of blue was a little bit discolored.

An Ink having the composition of Example 13 (FIG. 20) and further being mixed with 3.0 parts by weight of 4,4'-(1-α-methylbenzylidene)bisphenol as a polyphenol compound which has an effect of preventing discoloration of a sample in highly humid surroundings after sterilization treatment and also has an effect of somewhat enhancing coloration during plasma sterilization was prepared, and then this ink was applied onto YUPO (polypropylene synthetic paper) and Tyvek by hand, and an indicator for plasma sterilization (Example 14 (FIG. 21)) was prepared.

This indicator was slightly of color in contrast to the indicator of Example 13 (FIG. 20) due to mixing of 4,4'-(1-α-methylbenzylidene)bisphenol which is a polyphenol compound, and when this indicator was subjected to sterilization treatment with the plasma sterilizer manufactured by Johnson & Johnson Medical, the samples of this indicator changed color in blue with somewhat higher color density than the sample of Example 13 (FIG. 20).

When a test was performed wherein the samples of this indicator of Example 14 (FIG. 21) after sterilization treatment are left in a constant temperature and constant humidity bath at a temperature of 40° C. and at a humidity of 90% RH for 1 week, little discoloration was observed.

Using the following agents, as a pigment, 0.5 parts by weight of PSD-3G (produced by Nippon Soda) which is a colorless fluoran pigment; as a coloring assistant, 0.4 parts by weight of 2-amino-5-mercapto-1,3,4-thiadiazole; as a binder, 12.5 parts by weight of vinyl butyral resin (Esrek BM-5 produced by Sekisui Chemical); and as a solvent, about 85 parts by weight of methyl ethyl ketone, an ink was prepared, and then, the ink was applied onto a base material made of Tyvek (polyethylene synthetic paper) with a 0.25 m/m wire bar by hand, and an indicator for plasma sterilization of Example 15 (FIG. 22) was prepared.

This indicator was almost colorless, and when this indicator was subjected to sterilization treatment with the plasma sterilizer manufactured by Johnson & Johnson Medical under the standard condition, the sample was colored dark green.

When a test was performed wherein the sample after sterilization is left in a constant temperature and constant humidity bath at a temperature of 40° C. and at a humidity of 90% RH for 1 week, no discoloration was observed.

Using the following agents, as a pigment, 0.5 parts by weight of TH-107 (produced by Hodogaya Chemical Industry, FIG. 7) which is a colorless fluoran pigment; as a coloring assistant, 1.6 parts by weight of tetraethylthiuram disulfide which is a compound having a dithiocarbamyl group in Example 16 (FIG. 23), 1.6 parts by weight of tetra-n-butylthiuram disulfide which is a compound having a dithiocarbamyl group in Example 17 (FIG. 24), 1.6 parts by weight of 2-benzothiazolyl diethyldithiocarbamate which is a compound having a dithiocarbamyl group in Example 18 (FIG. 25); as a discoloration preventing agent for a colored pigment by sterilization treatment, 4.0 parts by weight of 1,1-bis(4-hydroxyphenyl)cyclohexane which is a polyphenol compound; as a binder, 12.5 parts by weight of ethyl cellulose (Ethocell No. 4 produced by Dow Chemical); and as a solvent, about 85 parts by weight of a mixture of methyl ethyl ketone and toluene (9:1), inks were prepared, and then, each of the inks was applied onto a base material made of polyethylene synthetic paper (Tyvek produced by Du Pont) with a 0.25 m/m wire bar by hand, and indicators for plasma sterilization were prepared.

Each of the samples of Example 16 (FIG. 23), Example 17 (FIG. 24) and Example 18 (FIG. 25) was colorless, and when the samples were subjected to sterilization treatment with the plasma sterilizer STERRAD 100 manufactured by Johnson & Johnson Medical under the standard condition, each of the samples changed color in black (were colored black).

Additionally, when these indicators were exposed to a hydrogen peroxide vapor (at around room temperature), the color density of the sample of Example 16 (FIG. 23) was enhanced after about 20 min, and after 1 hour, was colored black of almost saturated color density (almost the same level as color density after plasma sterilization treatment as mentioned above), and from then on, the color density remained unchanged. Furthermore, with regard to the samples of Example 17 (FIG. 24) and Example 18 (FIG. 25), a coloration rise was slow, and the coloration hardly proceeded for nearly 3 hours, and the coloration proceeded approximately after 3 hours passed, and after 4 hours, it was colored black of almost saturated color density, and from then, the color density remained constant.

Using the following agents:

(1) as a pigment, 0.2 parts by weight of NC-Blue-5 (produced by Hodogaya Chemical Industry) which is a colorless fluoran pigment, and 0.05 parts by weight of a carbinol base of Pararosaniline (a triphenylmethane basic pigment) which is discolored (loses color) by plasma sterilization in the presence of the following coloring assistant;

(2) as a coloring assistant, 2.5 parts by weight of tetraethylthiuram disulfide;

(3) as a binder, 12.5 parts by weight of ethyl cellulose (Ethocell No. 4 produced by Dow Chemical); and (4) as a solvent, about 85 parts by weight of a methyl ethyl ketone, an ink was prepared, and then, the ink was applied onto a base material of Tyvek (polyethylene synthetic paper) with a 0.25 m/m wire bar by hand, and an indicator for plasma sterilization of Example 19 (FIG. 26) was prepared.

The color tone of this indicator before sterilization was pinkish red, and when this indicator was subjected to sterilization treatment with the plasma sterilizer manufactured by Johnson & Johnson Medical under the standard condition, the sample changed color in blue.

In order to investigate a discoloration property of the sample after sterilization treatment in highly humid surroundings, a test was performed wherein the sample after sterilization is left in a constant temperature and constant humidity bath at a temperature of 40° C. and at a humidity of 90% RH for 1 week, however, discoloration was recognized to a certain extent.

An Ink having the composition of Example 19 (FIG. 26) and in addition, being mixed with 5.0 parts by weight of 4,4'-(1-α-methylbenzylidene)bisphenol as a polyphenol compound which has an effect of allowing a sample in highly humid surroundings after sterilization treatment to be resistant to discoloration and also has an effect of somewhat increasing coloration during plasma sterilization was prepared, and then this ink was applied onto Tyvek by hand, and an indicator for plasma sterilization of Example 20 (FIG. 27) was prepared.

This indicator was pinkish red with somewhat higher color density than the indicator of Example 19 (FIG. 26), and when this indicator was subjected to sterilization treatment with the plasma sterilizer manufactured by Johnson & Johnson Medical under the standard condition, the sample of this indicator changed color in blue with further somewhat higher color density than the indicator of Example 19 (FIG. 26).

In order to investigate a discoloration property of the sample after sterilization treatment in highly humid surroundings, a test was performed wherein the sample after sterilization is left in a constant temperature and constant humidity bath at a temperature of 40° C. and at a humidity of 90% RH for 1 week, however, no discoloration was observed.

Using the following agents:

(1) as a pigment, 0.5 parts by weight of PSD-HR (produced by Nippon Soda) which is a colorless fluoran pigment, and in addition to this, 0.05 parts by weight of a carbinol base of Victoria Blue (a triphenylmethane basic pigment) which is a blue pigment having a property of being discolored (losing color) by plasma sterilization in the presence of the following coloring assistant;

(2) as a coloring assistant,
2.5 parts by weight of tetraethylthiuram disulfide;

(3) as a binder,
12.5 parts by weight of ethyl cellulose (Ethocell No. 4 produced by Dow Chemical); and (4) as a solvent,
about 85 parts by weight of a methyl ethyl ketone, an ink was prepared, and then, the ink was applied onto a base material of Tyvek with a 0.25 m/m wire bar by hand, and an indicator for plasma sterilization of Example 21 (FIG. 28) was prepared.

This indicator showed light blue, and when this indicator was subjected to sterilization treatment with the plasma sterilizer manufactured by Johnson & Johnson Medical under the standard condition, the sample changed color in red.

When a test was performed wherein the sample of this indicator after sterilization treatment is left in a constant temperature and constant humidity bath at a temperature of 40° C. and at a humidity of 90% RH for 1 week, no discoloration was observed.

An Ink having the above-mentioned composition and in addition, being mixed with 5.0 parts by weight of 1,1'-bis(4-hydroxyphenyl)cyclohexane as a polyphenol compound which has an effect of allowing a sample in highly humid surroundings after sterilization treatment to be resistant to discoloration and an effect of somewhat increasing coloration during plasma sterilization was prepared, and then this ink was applied onto Tyvek by hand, and an indicator for plasma sterilization of Example 22 (FIG. 29) was prepared.

This indicator was somewhat deeper light blue than the indicator of Example 21 (FIG. 28), and when this indicator was subjected to sterilization treatment with the plasma sterilizer manufactured by Johnson & Johnson Medical under a condition similar to in Example 21 (FIG. 28), the sample of this indicator changed color in red with somewhat higher color density than the indicator of Example 18 (FIG. 25).

When a test was performed wherein the sample of this indicator after sterilization treatment is left in a constant temperature and constant humidity bath at a temperature of 40° C. and at a humidity of 90% RH for 1 week, no discoloration was observed.

Indicators (Comparative Example 13 to Comparative Example 16) were prepared using, as a pigment, colorless pigments other than fluoran pigments.

Figure 2:
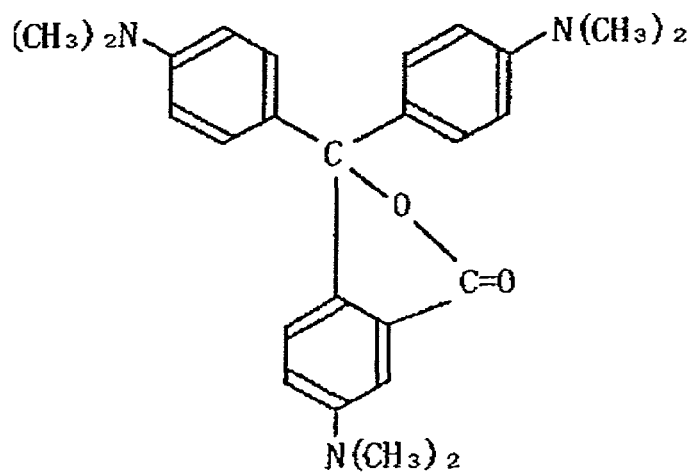
FIG. 2 illustrates a structural formula of Crystal Violet lactone which is a pigment.
Figure 3:
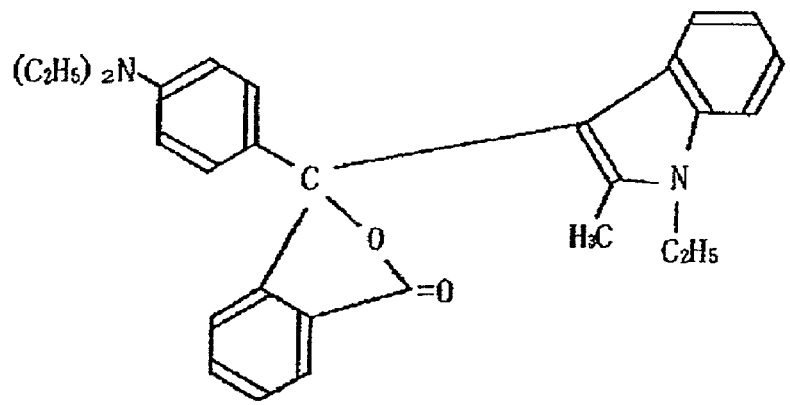
FIG. 3 illustrates a structural formula of Blue-200 which is a pigment.
Figure 4:
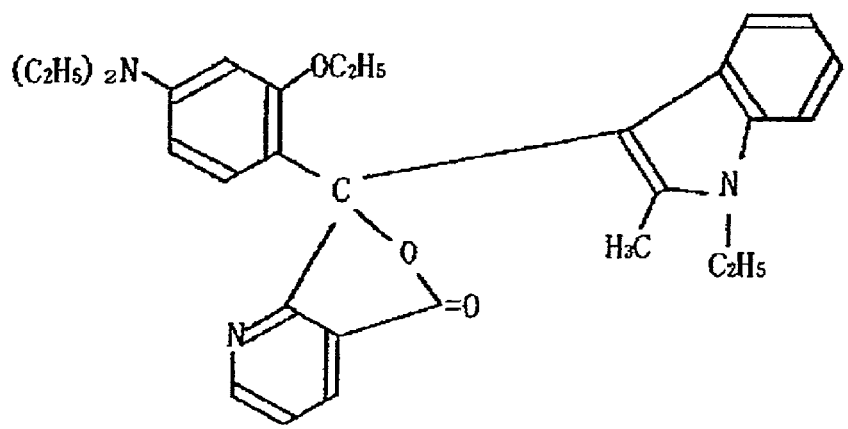
FIG. 4 illustrates a structural formula of Blue-63 which is a pigment.
Figure 5:
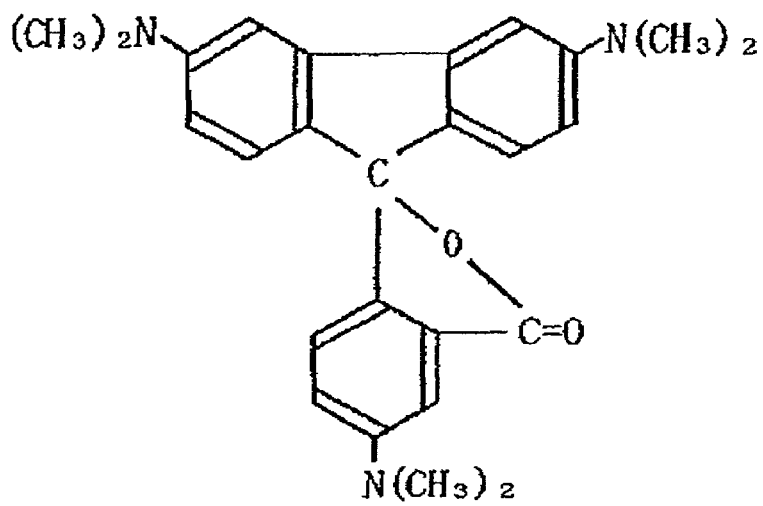
FIG. 5 illustrates a structural formula of G-118 which is a pigment.

Using the following pigments:
as a pigment,
0.3 parts by weight of 3,3-bis(p-dimethylaminophenyl)-6-dimethylamonophthalide (Crystal Violet lactone: FIG. 2) in Comparative Example 13,
0.4 parts by weight of Blue-200 (produced by Hodogaya Chemical: FIG. 3) in Comparative Example 14,
0.4 parts by weight of Blue-63 (produced by Yamamoto Chemical: FIG. 4) in Comparative Example 15, and
0.5 parts by weight of G-118 (produced by Yamamoto Chemical: FIG. 5) in Comparative Example 16,
inks were prepared with a composition similar to that in Example 2 (FIG. 9), and then each of the inks was applied onto a base material of Tyvek (polyethylene synthetic paper produced by Du Pont) with a 0.25 m/m wire bar by hand, and indicators for plasma sterilization of Comparative Example 13 to Comparative Example 16 were prepared.

Each of the indicators for plasma sterilization was almost colorless, and when these were subjected to sterilization treatment under the same condition as in Example 2 (FIG. 9) with the plasma sterilizer manufactured by Johnson & Johnson Medical, each of the samples of Comparative Examples hardly changed color (was hardly colored).

Inks having the compositions of Comparative Example 13 to Comparative Example 16 and in addition, being mixed with 5 parts by weight of 1,1-bis(4-hydroxyphenyl)cyclohexane as a polyphenol compound, respectively, were prepared, and then, these inks were applied onto Tyvek by hand, and indicators for plasma sterilization (Comparative Examples 17 to 20) were prepared.

These indicators for plasma sterilization were slightly of color because the colorless pigments of them were only partly colored due to mixing of 1,1-bis(4-hydroxyphenyl)cyclohexane that is a polyphenol compound, and when these were subjected to sterilization treatment with the plasma sterilizer manufactured by Johnson & Johnson Medical, the samples of Comparative Examples were hardly colored, which were scarcely different from the samples of Comparative Examples 13 to 16.

The above-mentioned Comparative Example 1 to Comparative Example 20 were as follows. In Comparative Example 1 to Comparative Example 12, inks have the compositions used in Example 1 to Example 12 except that the coloring assistants are not mixed. With regard to ingredients (a pigment, a discoloration preventing agent, a binder and a solvent) other than a coloring assistant, the inks have the similar compositions.

Comparative Example 1 is equivalent to Example 1 with the exception of a coloring assistant.

Comparative Example 2 is equivalent to Example 2 with the exception of a coloring assistant.

Comparative Example 3 is equivalent to Example 3 with the exception of a coloring assistant.

Comparative Example 4 is equivalent to Example 4 with the exception of a coloring assistant.

Comparative Example 5 is equivalent to Example 5 with the exception of a coloring assistant.

Comparative Example 6 is equivalent to Example 6 with the exception of a coloring assistant.

Comparative Example 7 is equivalent to Example 7 with the exception of a coloring assistant.

Comparative Example 8 is equivalent to Example 8 with the exception of a coloring assistant.

Comparative Example 9 is equivalent to Example 9 with the exception of a coloring assistant.

Comparative Example 10 is equivalent to Example 10 with the exception of a coloring assistant.

Comparative Example 11 is equivalent to Example 11 with the exception of a coloring assistant.

Comparative Example 12 is equivalent to Example 12 with the exception of a coloring assistant.

In Comparative Example 13 to Comparative Example 16, compositions of inks are different from those used in Example 2 only with regard to a pigment, and are similar to those of Example 2 except a pigment. Pigments used here are pigments other than fluoran pigments and inks were prepared by mixing respectively, 0.3 parts by weight of 3,3-bis(p-dimethylaminophenyl)-6-dimethylaminophthalide (Crystal Violet lactone) in Comparative Example 13, 0.4 parts by weight of Blue-200 in Comparative Example 14, 0.4 parts by weight of Blue-63 in Comparative Example 15, and 0.5 parts by weight of G-118 in Comparative Example 16.

In Comparative Example 17 to Comparative Example 20, Inks have the compositions similar to those of Comparative Example 13 to Comparative Example 16 and in addition, being further mixed with 5 parts by weight of 1,1-bis(4-hydroxyphenyl)cyclohexane as a discoloration preventing agent.

Inks were prepared by mixing:

5 parts by weight of a discoloration preventing agent 1,1-bis(4-hydroxyphenyl)cyclohexane into the ink of Comparative Example 13, in Comparative Example 17, 5 parts by weight of a discoloration preventing agent 1,1-bis(4-hydroxyphenyl)cyclohexane into the ink of Comparative Example 14, in Comparative Example 18, 5 parts by weight of a discoloration preventing agent 1,1-bis(4-hydroxyphenyl)cyclohexane into the ink of Comparative Example 15, in Comparative Example 19, and 5 parts by weight of a discoloration preventing agent 1,1-bis(4-hydroxyphenyl)cyclohexane into the ink of Comparative Example 16, in Comparative Example 20.

EFFECTS OF THE INVENTION

As described above, an indicator for plasma sterilization prepared by applying the present invention has the following effects.

Firstly, if the indicator which is applied to or printed on the surface of packaging materials for sterilization made of materials such as sterilized paper and the like, is used, a determination whether objects to be sterilized have experienced a sterilization process can be made on the basis of the color.

Secondly, if the indicator which is printed on cards and the like, is subjected to sterilization treatment with objects to be sterilized, whether sterilization conditions applied to the objects have been appropriate can be detected on the basis of the color tone change after sterilization.

Thirdly, an indicator which has the following features in quality can be prepared. Namely, (1) since colorless fluoran pigments include pigments which are colored in various color tones, an indicator which changes color in an arbitrary color tone can be prepared by selecting the pigments. Moreover, (2) by changing types and mixing amounts of the coloring assistants, indicators which have different speeds of color change (coloration) during sterilization treatment can be also prepared. In particular, by using as a coloring assistant an appropriate amount of a compound having a dithiocarbamyl, which has a low coloration promoting property in a hydrogen peroxide vapor, it is possible to prepare an indicator which slowly changes color (is slowly colored) in a diffusion step of diffusing a hydrogen peroxide vapor in a plasma sterilization process, and which rapidly changes color (is colored rapidly) in a plasma generation step (an indicator which changes color in proportion to the sterilization effect).

Furthermore, (3) in combination with the colorless fluoran pigment, by using a pigment which has the property of discoloring (losing color) by a plasma sterilization treatment in the presence of a coloring assistant, an indicator which is colored from one arbitrary color tone to another arbitrary color tone can be prepared.

The invention claimed is:

1. An indicator for plasma sterilization, comprising
   at least one type of colorless chromogenic fluoran pigment,
   a coloring assistant,
   a binder, and
   a discoloration preventing agent for pigment colored by plasma sterilization and comprising a polyphenol compound,
   wherein the color change of the indicator is allowed to occur by the low temperature plasma sterilization.

2. An indicator for plasma sterilization comprising an ink containing
   at least one type of colorless chromogenic fluoran pigment,
   a coloring assistant comprising at least one compound having a dithiocarbamyl group,
   a binder for base material, and
   a discoloration preventing agent for pigment colored by the hydrogen peroxide plasma sterilization and comprising a polyphenol compound,
   wherein said indicator is formed to undergo color tone change by hydrogen peroxide low temperature plasma sterilization.

3. The indicator of claim 1, wherein said at least one of polyphenol compound is selected from the group consisting of
   diphenol acid;
   phenolphthalein;
   bis(4-hydroxyphenyl)propane;
   1,1-bis(4-hydroxyphenyl)cyclohexane;
   bis(4-hydroxyphenyl)sulfone;
   bis(4-hydroxyphenyl)sulfide;
   9,9-bis(4-hydroxyphenyl)fluorene;
   4,4'-(1-α-methylbenzylidene)bisphenol;
   α, α'-bis(4-hydroxyphenyl)-1,4-diisopropylbenzene;
   4,4'-bisbutlylidenebis(3-methyl-6-tertbutylphenol);
   α,α,α'-tris(4-hydroxyphenyl)-1-ethyl-4-isopropylbenzene;

oligomers of 4-phenylphenol and formaldehyde; and polyvinylphenol(poly(p-hydroxystyrene)).

4. The indicator of claim 2, wherein said coloring assistant additionally includes at least one compound having a mercapto group.

5. The indicator of claim 2, wherein said at least one compound having the dithiocarbamyl group exhibits coloration promoting property in hydrogen peroxide vapor.

6. The indicator for plasma sterilization of claim 1, wherein the low temperature plasma sterilization is hydrogen peroxide low temperature plasma sterilization.

7. The indicator for plasma sterilization of claim 2, wherein the low temperature plasma sterilization is hydrogen peroxide low temperature plasma sterilization.

\* \* \* \* \*